United States Patent [19]

Keyworth et al.

[11] 4,014,950

[45] Mar. 29, 1977

[54] PROCESS FOR THE PURIFICATION OF LIQUID SORBENTS COMPRISING BIMETALLIC SALT COMPLEXES

[75] Inventors: Donald A. Keyworth, Houston; Jerome R. Sudduth, Pasadena, both of Tex.

[73] Assignee: Tenneco Chemicals, Inc., Saddle Brook, N.J.

[22] Filed: July 2, 1975

[21] Appl. No.: 592,564

[52] U.S. Cl. .......................... 260/677 A; 260/430; 260/438.1; 423/245

[51] Int. Cl.² ......................................... C07C 11/02

[58] Field of Search ............................. 260/677 A

[56] References Cited

UNITED STATES PATENTS

| | | | |
|---|---|---|---|
| 3,592,865 | 7/1971 | Long et al. | 260/677 A |
| 3,923,958 | 12/1975 | Turnbo et al. | 260/677 A |

*Primary Examiner*—Herbert Levine
*Attorney, Agent, or Firm*—Evelyn Berlow

[57] ABSTRACT

Liquid sorbents that are solutions in an aromatic hydrocarbon or halogenated aromatic hydrocarbon of a bimetallic salt complex having the generic formula $M_I \cdot M_{II} X_n \cdot$Aromatic, wherein $M_I$ is a Group I-B metal, $M_{II}$ is a Group III-A metal, X is halogen, $n$ is the sum of the valences of $M_I$ and $M_{II}$, and Aromatic is a monocyclic aromatic hydrocarbon or halogenated aromatic hydrocarbon having 6 to 12 carbon atoms and that contain as impurities polyalkylated aromatic compounds and/or olefin oligomers are purified by contacting them with an organic solvent in which the impurities are soluble and with which the liquid sorbents are immiscible. Suitable organic solvents include paraffinic hydrocarbons having 5 to 14 carbon atoms.

7 Claims, No Drawings

PROCESS FOR THE PURIFICATION OF LIQUID SORBENTS COMPRISING BIMETALLIC SALT COMPLEXES

This invention relates to a process for the purification of liquid sorbents that are used to separate olefins from gas streams. More particularly, it relates to a process for the separation of polyalkylated aromatic compounds and/or olefin oligomers from liquid sorbents that contain certain bimetallic salt complexes.

Bimetallic salt complexes that have the generic formula $M_I M_{II} X_n$.Aromatic, wherein $M_I$ is a Group I-B metal, $M_{II}$ is a Group III-A metal, X is halogen, $n$ is the sum of the valences of $M_I$ and $M_{II}$, and Aromatic is a monocyclic aromatic hydrocarbon or halogenated aromatic hydrocarbon having 6 to 12 carbon atoms, are known to be useful in the separation from gas mixtures of such complexible ligands as olefins, acetylenes, aromatics, and carbon monoxide. For example, in U.S. Pat. No. 3,651,159, Long et al. disclosed a process in which a sorbent solution of cuprous aluminum tetrahalide in toluene was used to separate ethylene, propylene, and other complexible ligands from a feedstream. The complexed ligands were recovered by ligand exchange with toluene. The resulting solution of cuprous aluminum tetrahalide in toluene was recycled and used to separate additional quantities of the complexible ligands from the feedstream.

In processes such as that disclosed by Long et al. in which a liquid sorbent containing a bimetallic salt complex is recycled without purification and is used for long periods of time, there is a gradual increase in the amounts of reaction by-products and other impurities in it until sufficient impurities are present to interfere with the efficient operation of the process. For example, when the liquid sorbent is contacted with a gas stream that contains an olefin having 2 to 4 carbon atoms, some of the olefin undergoes polymerization to form olefin oligomers and some reacts with the aromatic hydrocarbon or halogenated aromatic hydrocarbon in the sorbent to form polyalkylated aromatic compounds. Attempts to inhibit the polymerization and alkylation reactions, for example, by the addition of ammonia or another basic compound to the sorbent, have been unsuccessful because they failed to reduce the amounts of by-products formed or because they interfered with the efficient operation of the process.

In accordance with this invention, it has been found that the polyalkylated aromatic compounds and olefin oligomers that are formed as reaction by-products when a gas feedstream that contains at least one olefin having 2 to 4 carbon atoms is contacted with a liquid sorbent that is a solution of the bimetallic salt complex $M_I M_{II} X_n$.Aromatic in an aromatic hydrocarbon or a halogenated aromatic hydrocarbon can be removed from the liquid sorbent by contacting the liquid sorbent with an organic solvent in which the reaction by-products are soluble and with which the liquid sorbent is immiscible. This purification process, which is inexpensive and simple to carry out, can be used to remove impurities from liquid sorbent that contains the olefin-bimetallic salt complex or from liquid sorbent from which the olefin has been separated. Liquid sorbent which has been purified in this way can be used for long periods of time without danger of formation of amounts of reaction by-products that interfere with the operation of the olefin separation procedure and make necessary the replacement of the liquid sorbent and the cleaning of the apparatus.

The liquid sorbents that are purified by the process of this invention are solutions of a bimetallic salt complex in an aromatic hydrocarbon or halogenated aromatic hydrocarbon that contain polyalkylated aromatic compounds and/or olefin oligomers. The bimetallic salt complexes in the liquid sorbents have the generic formula $M_I M_{II} X_n$.Aromatic. $M_I$ is a Group I-B metal; that is, copper, silver, or gold. Copper (I) is the preferred metal. $M_{II}$ is a Group III-A metal; that is boron, aluminum, gallium, indium, or thallium. Boron and aluminum are the preferred metals, aluminum being particularly preferred. X is halogen, i.e., fluorine, chlorine, bromine, or iodine; it is preferably chlorine or bromine. The sum of the valences of $M_I$ and $M_{II}$ is represented by $n$. Aromatic is a monocyclic aromatic hydrocarbon or halogenated aromatic hydrocarbon having 6 to 12 carbon atoms, and preferably 6 to 9 carbon atoms, such as benzene, toluene, ethylbenzene, xylene, mesitylene, chlorobenzene, bromobenzene, iodobenzene, chlorotoluene, bromotoluene, iodotoluene, or chloroxylene. It is preferably toluene. Illustrative of these bimetallic salt complexes are the following: $CuBF_4$.benzene, $CuBCl_4$.benzene, $AgBF_4$.mesitylene, $AgBCl_4$.xylene, $AgAlCl_4$.xylene, $AgAlBr_4$.benzene, $CuGaCl_4$.toluene, $CuInI_4$.chlorobenzene, $CuThI_4$. p-chlorotoluene, and the like. The preferred bimetallic salt complexes are $CuAlCl_4$.toluene and $CuAlBr_4$.toluene. The aromatic hydrocarbon in which the bimetallic salt complex is dissolved is usually and preferably the same as that used in the preparation of the bimetallic salt complex, but if desired it may be a different one. The total amount of aromatic hydrocarbon in the liquid sorbent, that is, the amount in the bimetallic salt complex plus the amount used as solvent, is at least 10 mole percent of the amount of the bimetallic salt $M_I M_{II} X_n$ that is present. It is preferred that the amount of aromatic hydrocarbon be 100 to 450 mole percent of the amount of the bimetallic salt. The particularly preferred liquid sorbents contain 25 to 75 percent by weight of $CuAlCl_4$.toluene in toluene.

The organic solvents that can be used to remove polyalkylated aromatic compounds and/or olefinic oligomers from liquid sorbents are those in which the polyalkylated aromatic compounds and the olefin oligomers are soluble and with which the liquid sorbent is immiscible. The preferred organic solvents are straight-chain and branched-chain paraffinic hydrocarbons having from 5 to 14 carbon atoms. These include n-pentane, isopentane, n-hexane, isohexane, 3-methylpentane, 2,2-dimethylbutane, 2,3-dimethylbutane, n-heptane, isoheptane, 3,4-dimethylpentane, n-octane, 2-ethylhexane, n-decane, isodecane, n-dodecane, 2-ethyldecane, n-tetradecane, and mixtures thereof. Particularly good results have been obtained when n-hexane or n-heptane was used. The amount of organic solvent that is used in the purification process is not critical. In most cases, from 0.1 part to 10 parts by volume of organic solvent is used per part by volume of liquid sorbent. Particularly advantageous results have been obtained when from 0.5 part to 3 parts by volume of the organic solvent was used per part by volume of liquid sorbent.

When a gas feedstream that contains at least one olefin having 2 to 4 carbon atoms and optionally one or more other complexible ligands is brought into contact with a liquid sorbent that is a solution of the bimetallic salt complex $M_lM_{ll}X_n$. Aromatic in an aromatic hydrocarbon, the olefin and any other complexible ligands in the feedsteam react with the liquid sorbent to form reaction mixtures that comprise complexes of these ligands with the bimetallic salt complex. The reaction mixture is then heated or treated with another complexible ligand to displace the olefin and other complexible ligands from it. The stripped liquid sorbent is then recycled to the system where it is used to remove additional amounts of olefins and other complexible ligands from the gas feedstream.

In addition to reacting with the liquid sorbent to form complexes, the olefins in the gas feedstream react with the aromatic hydrocarbon or halogenated aromatic hydrocarbon in the liquid sorbent to form polyalkylated aromatic compounds that have the structural formula

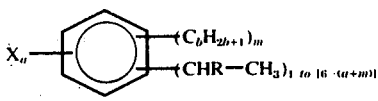

wherein X represents halogen; R represents hydrogen, methyl, or ethyl; $b$ represents 1 or 2; and $a$ and $m$ each represents 0,1, or 2. When the aromatic hydrocarbon in the liquid sorbent is toluene, the polyalkylated aromatic compounds have the structural formula

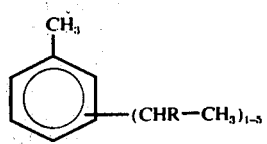

When the number of alkyl substituents on the aromatic ring is four or more, the polyalkylated compounds have only slight solubility in the liquid sorbent, and they tend to form deposits in the cooler parts of the apparatus. Unlike the mono-, di-, and trialkylated compounds, the polyalkylated aromatic compounds are too high boiling to be useful as the stripping gas that separates the olefins from the liquid sorbent.

The olefins also undergo polymerization in the liquid sorbent to form olefin oligomers that have molecular weights in the range of about 100 to 1000 and that have only limited solubility in the liquid sorbent.

The alkylation and polymerization reactions that yield the reaction by-products are catalyzed by the small amounts of aluminum chloride and other acidic compounds that are present in the liquid sorbent. They are also promoted by the elevated temperatures that are often used to decomplex the relatively-stable complexes formed by the olefins and the bimetallic salt complex.

In the purification process of this invention, the liquid sorbents that contain the aforementioned bimetallic salt complexes and impurities that are polyalkylated aromatic compounds and/or olefin oligomers are contacted with an organic solvent in which the impurities are soluble and with which the liquid sorbent is immiscible. A two-phase system is formed. The upper phase is a solution of a major amount of the impurities in the organic solvent; the lower phase is liquid sorbent that contains only a small amount of the impurities. The sorbent phase may be separated and returned to the system where it is used to remove additional amounts of olefin from the gas feedstream.

The organic solvent may be recovered from the solution containing the impurities, for example, by distillation. The residue, which contains polyalkylated aromatic compounds and olefin oligomers, has properties that make it valuable as a lubricant additive. Alternatively, it may be passed through a furnace to crack it to olefin and aromatic hydrocarbon, which can be recycled, or it may be burned for its fuel value.

The extraction of the reaction by-products from the liquid sorbent may be carried out at temperatures between about 10° and 90° C. It is usually and preferably carried out at ambient temperature.

The invention is further illustrated by the following examples.

EXAMPLE 1

A. A liquid sorbent that contained 28.6 mole percent of cuprous aluminum tetrachloride and 71.4 mole percent of toluene was prepared by adding 1.1 moles of cuprous chloride to 1 mole of anhydrous aluminum chloride in toluene. The resulting solution was filtered to remove unreacted cuprous chloride and insoluble impurities from it.

B. A gas feedstream, which had been obtained by the pyrolysis of naphtha, had after depropanization the following composition:

| | |
|---|---|
| Hydrogen | 3.5 mole percent |
| Methane | 3.8 |
| Ethylene | 48.3 |
| Ethane | 40.0 |
| Propylene | 1.5 |
| Propane | 0.3 |
| Butylenes and butanes | 1.3 |
| $C_5$ gasoline | 1.3 |

This gas was fed at ambient temperature and 19 psia into a column in which it was contacted with an amount of the liquid sorbent of Example 1A that contained at least sufficient cuprous aluminum tetrachloride to react with all of the olefins in the feedstream. The ethylene, propylene, and butylene in the feedstream reacted with the liquid sorbent as it traveled through the column to form a reaction mixture that was a solution of the ethylene-cuprous aluminum tetrachloride complex, the propylene-cuprous aluminum tetrachloride complex, and the butylene-cuprous aluminum tetrachloride complex in the liquid sorbent. This solution was fed to a stripping column in which it was brought into contact with benzene vapor at 95° C. The mixture of benzene vapor and olefins that left the column was cooled to separate the benzene from the olefins. The stripped liquid sorbent was returned to the column where it reacted with additional amounts of ethylene, propylene, and butylene in the gas feedstream.

C. After it had been used for several weeks in the process described in Example 1B, the liquid sorbent contained amounts of reaction by-products that interfered with its use in the removal of olefins from the gas feedstream.

This contaminated sorbent was contacted with an equal volume of n-hexane at ambient temperature. The resulting solution of the impurities in n-hexane was separated from the purified liquid sorbent. The purified liquid sorbent was recycled to the process and used in the process described in Example 1B. The solution containing the extracted impurities was heated to remove the hexane from it. The residue was a nonvolatile oil that was shown by analysis to be a mixture of polyalkylated toluenes, ethylene oligomers, propylene oligomers, and butylene oligomers.

EXAMPLE 2

A. A liquid sorbent that had a specific gravity of 1.185 was prepared by dissolving 1.05 moles (104 grams) of cuprous chloride and 1.00 mole (133 grams) of aluminum chloride in 3 moles (276 grams) of toluene. The mixture was stirred to dissolve the solids and heated to remove hydrogen chloride, which was produced from traces of water in the reagents.

B. A gas feedstream that contained 55.10 mole percent of ethane, 43.45 mole percent of ethylene, and 1.45 mole percent of acetylene was fed at the rate of 436 cc/min. into a column in which it was contacted with the liquid sorbent of Example 2A. The ethylene and acetylene in the feedstream reacted with the liquid sorbent to form complexes with the cuprous aluminum tetrachloride. The resulting reaction mixture was fed to a stripping column in which it was brought into contact with benzene vapor at 90° C. The mixture of benzene vapor, ethylene, and acetylene that left the column was cooled to separate the benzene from it. The stripped liquid sorbent was recycled to the absorption column to remove additional amounts of ethylene and acetylene from the feedstream.

After it had been used in this process for 118 hours, the liquid sorbent was extracted with twice its volume of n-heptane. From the n-heptane extract was recovered an oil that was shown by infrared analysis to be a mixture of ethylene oligomers and polyethylated toluene. Approximately 6% of the ethylene in the feedstream had been converted to these reaction by-products.

EXAMPLE 3

A gas feedstream that contained 26.1% of ethane, 26.2% of ethylene, and 47.7% of hydrogen was fed at the rate of 0.01 ft./minute for 144 hours to a column that contained 400 ml. of the liquid sorbent whose preparation is described in Example 2A.

At intervals, samples of the liquid sorbent were analyzed to determine the amount of ethylene that had undergone either oligomerization or alkylation. The following results were obtained:

| Time (Hours) | Ethylene Reaction Products in Liquid Sorbent (%) | Amount (%) of Ethylene Reacted | % of Ethylene Lost by Oligomerization | % of Ethylene Lost by Alkylation |
|---|---|---|---|---|
| 98 | 8.8 | 12.5 | 1.2 | 11.3 |
| 144 | 11.2 | 5.1 | 0.48 | 4.62 |

These data show that the ethylene loss is mainly due to alkylation of the aromatic compound in the liquid sorbent.

EXAMPLE 4

Propylene was fed for 24 hours to a column that contained 400 ml. of the liquid sorbent whose preparation is described in Example 2A. The propylene reacted with the liquid sorbent to form a solution of a propylene-cuprous aluminum tetrachloride complex in toluene; it also underwent polymerization and alkylation reactions. A total of 536 grams of propylene was fed into the column. When the liquid sorbent was stripped with n-hexane vapor, 134 grams of pure propylene was recovered. Extraction of the stripped liquid sorbent with n-hexane and removal of the n-hexane from the extract yielded 154 grams of an oil that contained a minor proportion of propylene oligomers and a major proportion of polypropylatedtoluene. This oil had the following properties:

| | |
|---|---|
| Molecular Weight (average) | 285 |
| Specific gravity | 0.852 |
| Reflux temperature (without decomposition) | 230° C. |

What is claimed is:

1. In the process for the separation of olefins having 2 to 4 carbon atoms from a gas feedstream wherein (a) the feedstream is contacted with a liquid sorbent that is a solution in an aromatic hydrocarbon or halogenated aromatic hydrocarbon of a bimetallic salt complex having the formula $$M_I M_{II} X_n \cdot \text{Aromatic}$$

wherein $M_I$ is a Group I-B metal, $M_{II}$ is a Group III-A metal, X is halogen, $n$ is the sum of the valences of $M_I$ and $M_{II}$, and Aromatic is a monocyclic aromatic hydrocarbon or halogenated aromatic hydrocarbon having 6 to 12 carbon atoms, thereby forming a reaction mixture that comprises a solution of a complex of the olefin and the bimetallic salt complex in the liquid sorbent, (b) the reaction mixture is separated from the feedstream, (c) the olefin is separated from the liquid sorbent in the reaction mixture, and (d) the liquid sorbent is recycled, the improvement that comprises removing from the liquid sorbent impurities selected from the group consisting of polyalkylated aromatic compounds, olefin oligomers, and mixtures thereof by contacting the liquid sorbent containing impurities with a sorbent-immiscible organic solvent that is a paraffinic hydrocarbon having 5 to 14 carbon atoms in the amount of from 0.1 part to 10 parts by volume of the sorbent-immiscible organic solvent per part by volume of liquid sorbent and thereafter separating a solution of the impurities in the sorbent-immiscible organic solvent from purified liquid sorbent.

2. The process of claim 1 wherein the sorbent-immiscible organic solvent is n-hexane.

3. The process of claim 1 wherein the sorbent-immiscible organic solvent is n-heptane.

4. The process of claim 1 wherein the liquid sorbent is a solution of cuprous aluminum tetrachloride.toluene in toluene.

5. The process of claim 1 wherein the olefins that are separated from the feedstream contain ethylene.

6. The process of claim 1 wherein the olefins that are separated from the feedstream contain propylene.

7. The process of claim 1 wherein the liquid sorbent containing said impurities is contacted with from 0.5 part to 3 parts by volume of the sorbent-immiscible organic solvent per part by volume of liquid sorbent.

* * * * *